(12) United States Patent
Pourdeyhimi et al.

(10) Patent No.: US 7,491,407 B2
(45) Date of Patent: Feb. 17, 2009

(54) FIBER-BASED NANO DRUG DELIVERY SYSTEMS (NDDS)

(75) Inventors: Behnam Pourdeyhimi, Cary, NC (US); Rory Holmes, Cary, NC (US); Trevor J. Little, Cary, NC (US)

(73) Assignee: North Carolina State University, Raleigh, NC (US)

(*) Notice: Subject to any disclaimer, the term of this patent is extended or adjusted under 35 U.S.C. 154(b) by 136 days.

(21) Appl. No.: 10/284,599

(22) Filed: Oct. 31, 2002

(65) Prior Publication Data
US 2003/0095998 A1 May 22, 2003

Related U.S. Application Data

(60) Provisional application No. 60/334,517, filed on Oct. 31, 2001.

(51) Int. Cl.
*A61K 9/70* (2006.01)

(52) U.S. Cl. .................................................. 424/443

(58) Field of Classification Search .................. 424/443
See application file for complete search history.

(56) References Cited

U.S. PATENT DOCUMENTS

| | | | |
|---|---|---|---|
| 5,200,194 A | * | 4/1993 | Edgren et al. ............... 424/473 |
| 5,456,923 A | | 10/1995 | Nakamichi et al. |
| 5,531,998 A | * | 7/1996 | Mares et al. ................ 424/426 |
| 5,650,170 A | * | 7/1997 | Wright et al. ............... 424/473 |
| 5,665,369 A | | 9/1997 | Wedlock et al. |
| 5,939,099 A | | 8/1999 | Grabowski et al. |
| 5,958,452 A | | 9/1999 | Oshlack et al. |
| 6,051,253 A | | 4/2000 | Zettler et al. |
| 6,083,430 A | * | 7/2000 | Fuisz et al. .................... 264/5 |
| 6,120,802 A | | 9/2000 | Breitenbach et al. |

\* cited by examiner

*Primary Examiner*—Humera N Sheikh
(74) *Attorney, Agent, or Firm*—Jenkins, Wilson, Taylor & Hunt, P.A.

(57) ABSTRACT

A drug delivery system in the form of homo-component, bi-component or multi-component fibers wherein one of more of the components comprise a drug compounded with a polymer carrier. These fibers are packed to form a tablet directly, or are chopped and placed in a capsule.

11 Claims, 17 Drawing Sheets

| | |
|---|---|
|  | Sheath Core |
|  | Eccentric Sheath Core |
|  | Side by Side |
|  | Three islands |
|  | Islands in the Sea |
|  | Segmented Pie (Pie Wedge) |
|  | Hollow Segmented Pie (Hollow Pie Wedge) |
|  | Tipped Trilobal Cross section |
|  | Segmented Ribbon |

FIBER-BASED NANO DRUG DELIVERY SYSTEMS (NDDS)

CROSS-REFERENCE TO RELATED APPLICATION

The present application claims priority to the U.S. provisional patent application Ser. No. 60/334,517, filed Oct. 31, 2001, and entitled "Drug Delivery System/Extruded Fiber," which application is incorporated herein by reference in its entirety.

FIELD OF THE INVENTION

The present invention relates to processes for creating extruded fibers containing a mixture of drugs and pharmaceutically acceptable polymers such that the drugs form nanofibers. The nanofibers of the present invention provide significant surface area allowing fast dissolution of the drugs. Means for directly forming such fibers into caplets or tablets are also an aspect of this invention.

BACKGROUND ART

The solubility behavior of a drug is a key determinant of its bioavailability. Solubility presents a challenge to the development of a suitable formulation for drugs. With the recent advent of high throughput screening of potential therapeutic agents, the number of poorly soluble drug candidates has risen sharply and the formulation of poorly soluble compounds now presents one of the most frequent and greatest challenges to formulation scientists in the pharmaceutical industry.

The production of drug delivery systems by melt extrusion of a polymer/active ingredient mixture is known in the art. In general, such processes Examples of such drug delivery systems are generally described in the U.S. patents set forth in Table 1.

TABLE 1

| U.S. Pat. No. | Title | Year |
|---|---|---|
| U.S. Pat. No. 5456923 | Method of manufacturing solid dispersion | 1995 |
| U.S. Pat. No. 5665369 | Fast-dispensing solid PVP-containing crop protection formulation and process | 1997 |
| U.S. Pat. No. 5939099 | Solid active extrusion compound preparations containing low-substituted hydroxypropylcellulose | 1999 |
| U.S. Pat. No. 5958452 | Extruded orally administrable opioid formulations | 1999 |
| U.S. Pat. No. 6051253 | Production of solid drug forms | 2000 |
| U.S. Pat. No. 6120802 | Method of producing multi-layer medicaments in solid form for oral or rectal administration | 2000 |

In general, the basic ingredients of a drug delivery system comprise (1) one or more pharmaceutically active ingredients (polymers); (2) one or more polymer binders; and (3) pharmaceutically acceptable ancillaries, plasticizers, and the like. Generally, active ingredients do not decompose at extrusion temperatures. Pharmaceutical auxiliaries may include plasticizers, fillers, lubricants, flow regulators, colorant, stabilizers, and the like, and are typically not affected by the process conditions. However, polymer carrier or binder components are preferably thermally stable so that they are not decomposed at extrusion temperatures. If such carriers or binder components are melt-extruded, they are preferably thermoplastic.

In general, the formulation of the polymer or the polymer mixture controls the active ingredient profile required by the end user. Examples of the manipulation of polymer carriers to control active ingredient profiles and release rates are set forth in, e.g., U.S. Pat. No. 5,665,369 to Wedlock (crop protection formulation, where rapid release is critical; PVP is used as a polymer binder); U.S. Pat. No. 5,939,099 to Grabowski (mixture of thermoplastic water soluble polymer and water insoluble, swellable, non-thermoplastic polymer L-HPC used to control the active ingredient release rate; and U.S. Pat. No. 5,958,452 to Oshlack (mixture of hydrophobic polymer and hydrophobic fusible carrier used in an orally administrable opioid formulation, where hydrophobic fusible carrier slows down the release of the active agents).

In general, the process for creating drug delivery systems to which the present invention relate comprises (1) a preparation step, wherein the ingredients of the drug mixture are mixed and melting or softened; (2) an extrusion step and, optionally, a (3) cooling or shaping step.

During the first preparation step, a common challenge is obtaining a homogeneous dispersion of the active ingredients in polymer binders. U.S. Pat. No. 5,456,592 to Nakamichi et al. describes the use of a twin-screw extruder to improve the process to obtain solid dispersion. "Solid dispersion" or "solid solution" generally refers to a mixture in which the active ingredient is present in the form of a molecular dispersion in the polymer. The twin-screw extruder consists of a metering feeder unit, a barrel, screws, exit dies, etc. Such extruders enhance the mixing process by creating high shear forces, transport capacity and compounding effects. Hence, the production of a solid dispersion can be obtained at lower temperature allowing the use of thermally sensitive ingredients. In addition, such extruders generate lower heats of friction than single screw extruders.

After preparation, drug mixtures are extruded through a suitable die. The mixture is melted or softened at the extrusion temperature. The shape of the die depends on the desired shape of drug formulation. Coextrusion dies may be used for multiple-layer drug production as set forth in U.S. Pat. No. 6,120,802 to Breitenbach.

The extruded drug mixture strand is solidified by cooling. The solid drug can be formed through a shaping process before or after the components are solidified. After cooling, the strand can be cut or divided into multiparticulates of desired size and divided into unit doses (see, e.g., U.S. Pat. No. 5,939,099). U.S. Pat. No. 6,051,253 to Zettler describes direct solid drug formation by splitting a drug mixture strand and then rounding-off the end of the strand before the extrudate is solidified. U.S. Pat. No. 6,120,802 to Breitenbach describes a one-step direct shaping process such that the extrudate is cut into the final tablet shape immediately after the extrusion, with the cutter/shaper being located downstream of the extruder die.

SUMMARY OF THE INVENTION

The following equation, based on the Noyes-Whitney equation, provides a general guideline as to how the dissolution rate of poorly soluble compounds may be improved:

$$\text{Rate of dissolution} = \frac{dC}{dt} = \frac{AD(C_s - C)}{h}$$

A=Surface Area
D=Diffusion Coefficient of the compound
C=Contentration of the drug at time t
h=Thickness of diffusion boundary layer According to this analysis, dissolution can be improved by increasing the surface area available for dissolution by decreasing the particle size of the solid compound and/or by optimizing the wetting characteristics of the compound surface, to decrease the boundary layer thickness, to ensure sink conditions for dissolution and to improve the apparent solubility of the drug under physiologically relevant conditions. This analysis provides a basis for this invention.

The present invention relates to the development of an extruded fiber-based nano drug delivery system (NDDS) by employing the extrusion of either a homocomponent fiber wherein the drug is mixed into the polymer carrier, or a bicomponent fiber wherein the drug is in one or both components, or a multi-component fiber wherein the drug and the carriers may be in one or more of the components. The bicomponent and multi-component fiber morphology allows the creation of very small extruded fibers with fiber diameters of less than 500 nanometers. In particular embodiments, one or more of the components is the active drug compounded together with a polymer carrier. One of the components may be a pharmaceutically acceptable polymer and may be the same as the polymer used for compounding the drug; alternatively, the polymer may be different than one used for compounding the drug.

In other aspects, the present invention relates to processes for the formation of tablets or caplets using extruded nanofibers.

DESCRIPTION OF THE DRAWINGS

Some of the objects of the invention having been stated other objects will become apparent with reference to the detailed description and the drawings as described hereinbelow.

DETAILED DESCRIPTION OF THE INVENTION

The invention is a fiber based nano drug delivery system. This invention addresses the development of the process for an extruded fiber-based nano drug delivery system (NDDS) by employing a homo-component, bi-component or multi-component fiber morphology wherein one or more of the components are the drug compounded together with a polymer carrier. Other components may be pure of compounded drug with a pharmaceutically acceptable polymer. The latter may be the same as the polymer used for compounding the drug or may be a different polymer.

Figure 1:
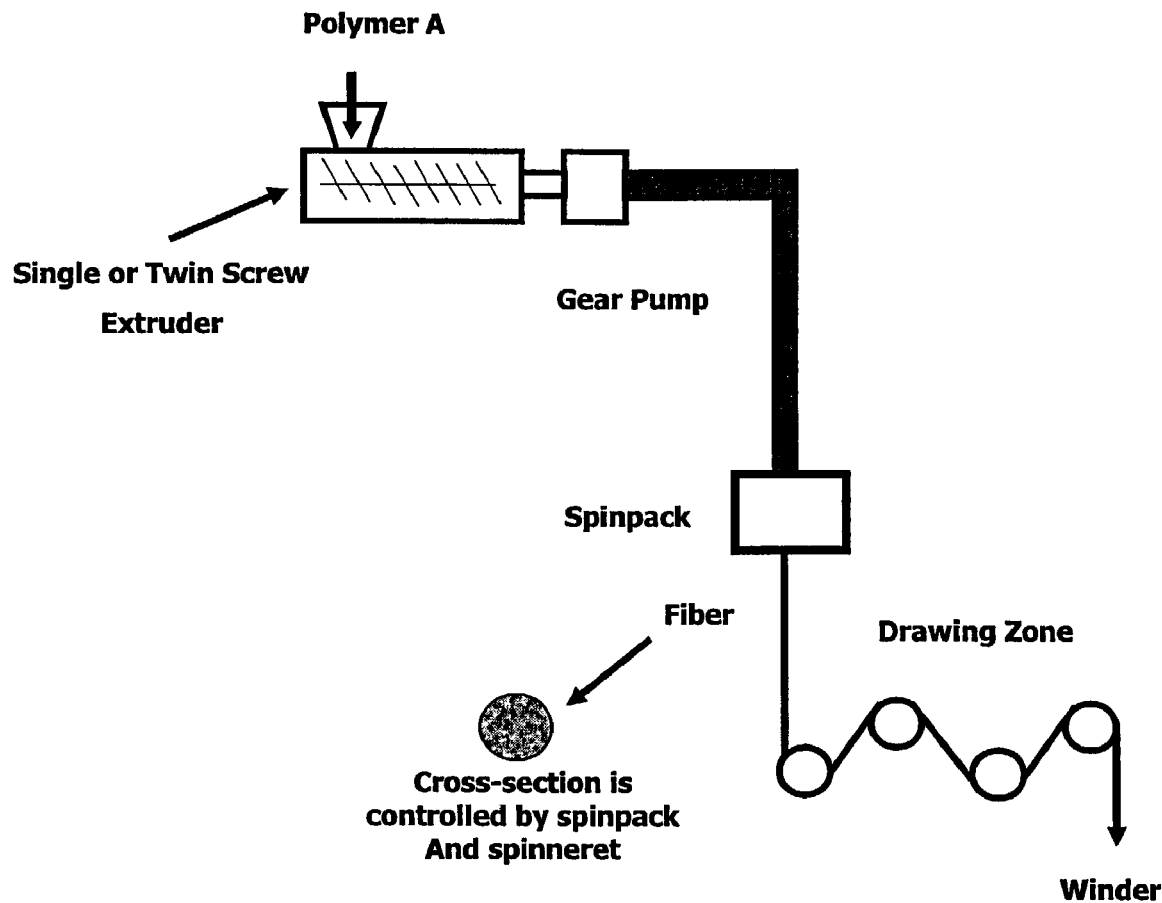
FIG. 1 is a schematic of a homo-component fiber spinning system. Preferably and typically, these fibers are larger than one micron.
Figure 2:
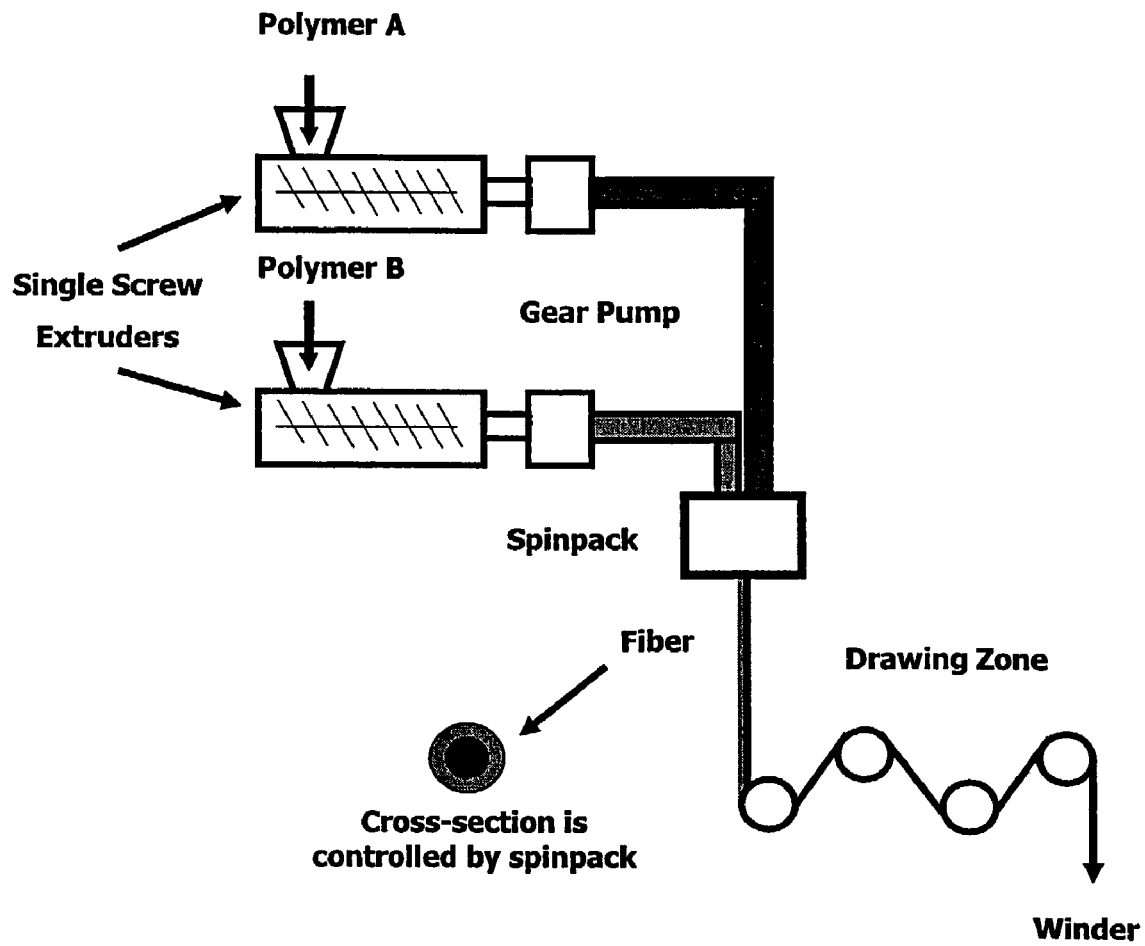
FIG. 2 is a schematic of a bicomponent fiber spinning system. Preferably and typically, these fibers can be smaller than one micron.
Figure 3:
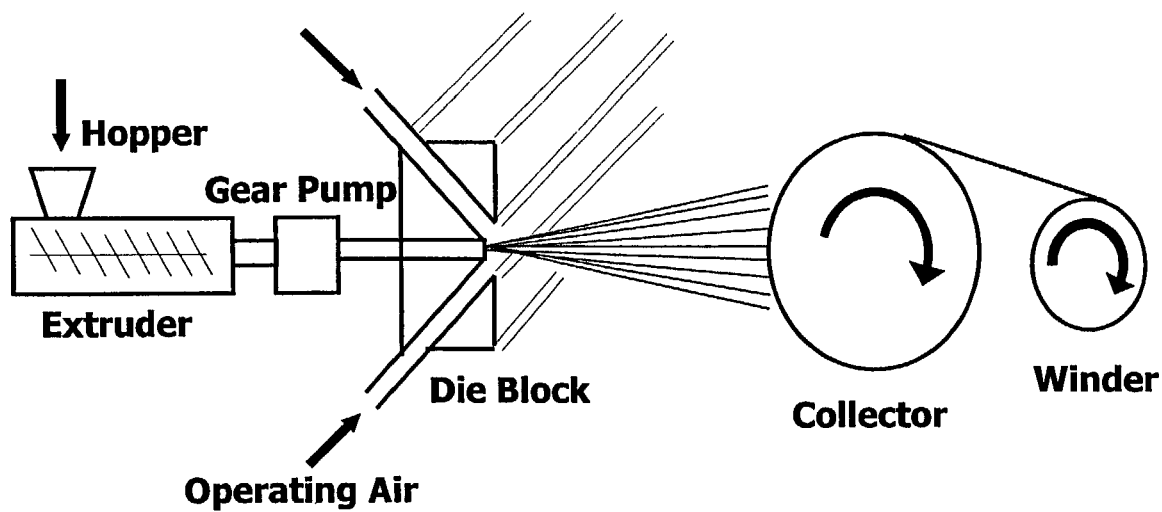
FIG. 3 is a schematic of a meltblowing process that may be used in one embodiment of the invention. The fibers illustrated herein may be less than 0.5 micron.

The extrusion processes for homo-component and bicomponent fibers are shown in FIGS. 1 and 2 and the process for meltblowing is depicted in FIG. 3. The manufacturing of the fiber based nano drug delivery system (NDDS) however, is not limited to these processes. Spunbonding, flash spinning, solvent spinning and solution blowing are other possible methods for the manufacturing of the fibers for NDDS.

The present invention relates to fibers with enhanced surface areas in order to accommodate and facilitate faster dissolution of the drug. In the present invention, the drug is included in a suitable polymer carrier by compounding and/or blending, extruding the blended or compounded material into fibers by extruding, thereby providing means for the delivery of the drug. The fibers will have enhanced areas in that the fibers have a rough cross section, or have a fiber size to below one micron.

Figure 4:
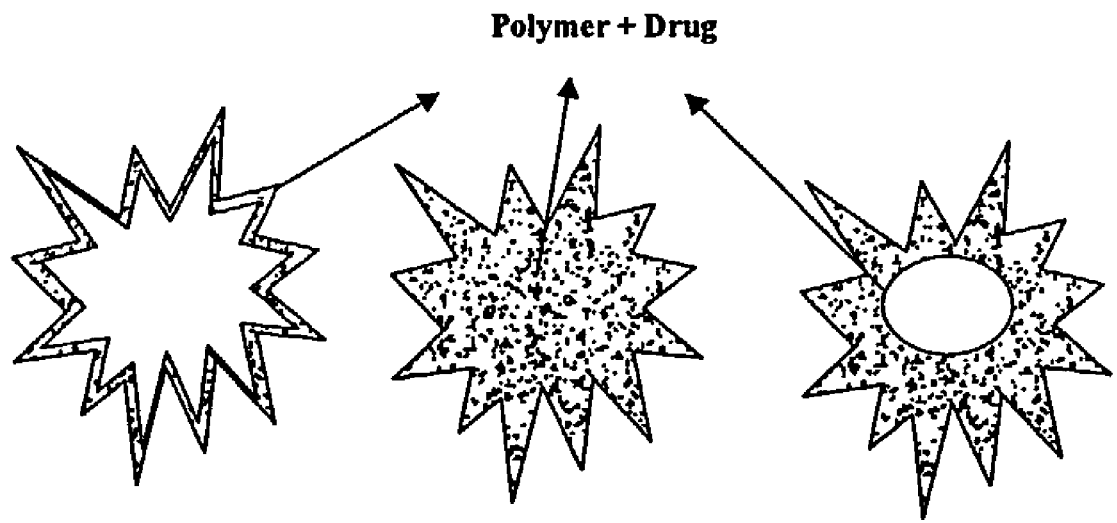
FIG. 4 is a schematic of homo-component fibers with high surface area that may be used in embodiments of the present invention.

FIG. 4 illustrates one embodiment in which the solubility of a homo-component fiber for NDDS is increased, and wherein the drug has been compounded into the fiber forming polymer. These fibers may be hollow, may have one or more holes and can be made by any of the well known extrusion processes.

Figure 5:
FIG. 5 is a schematic illustrating bicomponent fiber morphologies that may be used in the present invention.
Figure 5:
Figure 5:
Figure 5:
Figure 5:
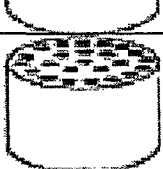
Figure 5:
Figure 5:
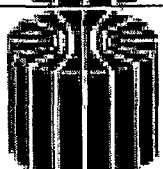
Figure 5:
Figure 5:

FIG. 5 shows various possible bicomponent configurations of the invention where the drug may be in one component.

Figure 6:
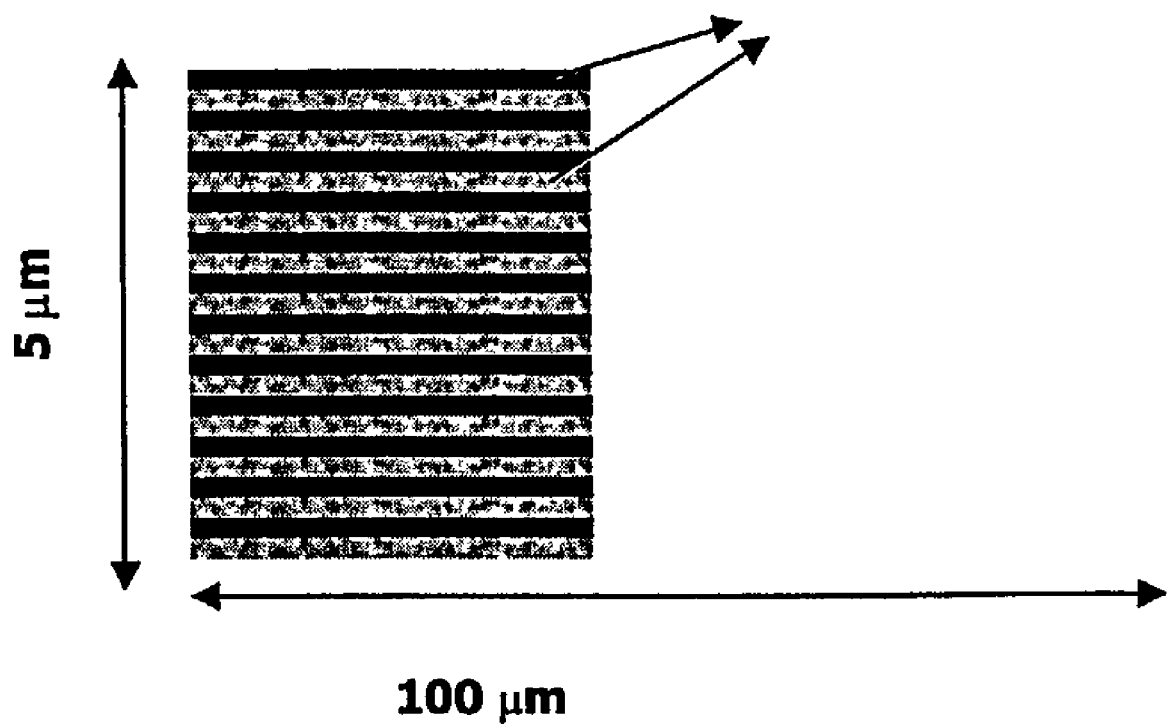
FIG. 6 is an example of an NDDS of the present invention having a stacked ribbon morphology.
Figure 7:
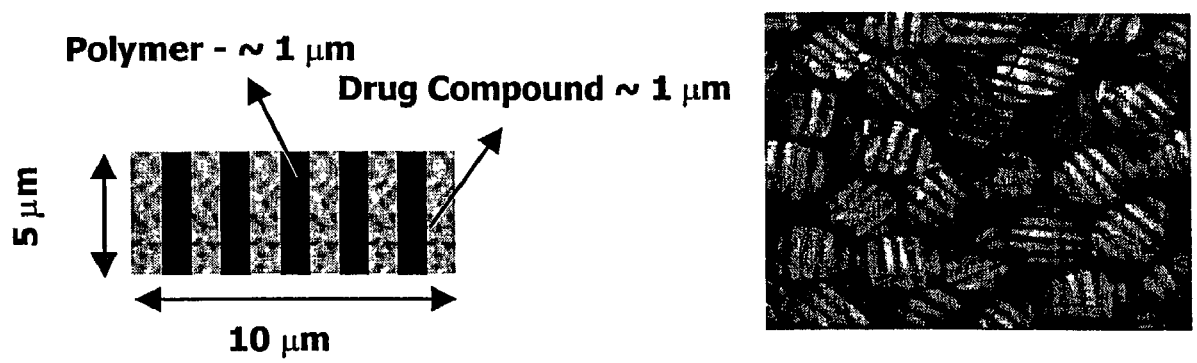
FIG. 7 is an example of an NDDS of the present invention having a ribbon morphology.

FIGS. 6 to 13 show the possibilities and the sizes that can be achieved by means of bicomponent fiber spinning. Multi-component fiber spinning can also be employed to form similar structures of similar dimension. In particular, FIG. 6 shows a stacked ribbon where the structure is composed of alternate layers of the drug compound and the pure polymer. These can be stacked to have as many as 48 layers or more. The thickness for each layer can be as little as 200 nanometers or less. Because these layers are stacked, there will be little or no tendency for the fibers to deform and join at the ends. This structure can also take the form of a ribbon. FIG. 7 shows one such possibility where the layers are in the form of a ribbon. A photomicrograph of a test specimen is also shown in FIG. 7 to the right of the fiber cross section.

Figure 8:
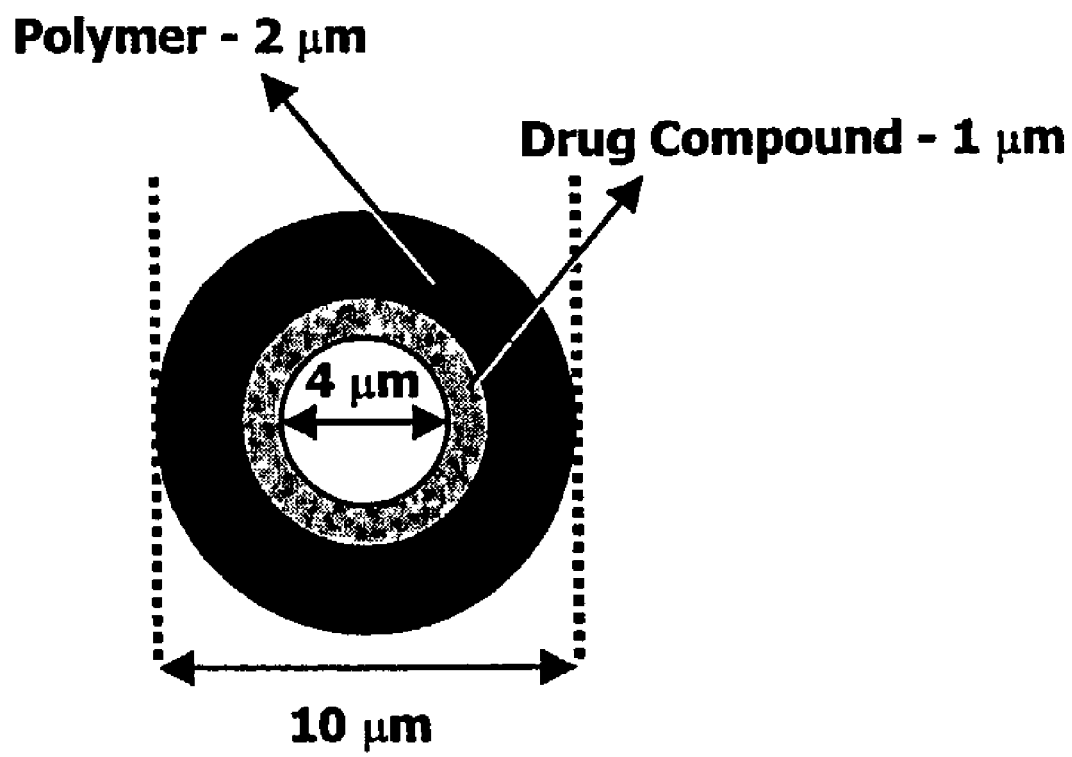
FIG. 8 is an example of an NDDS of the present invention having a hollow, sheath-core morphology.
Figure 9:
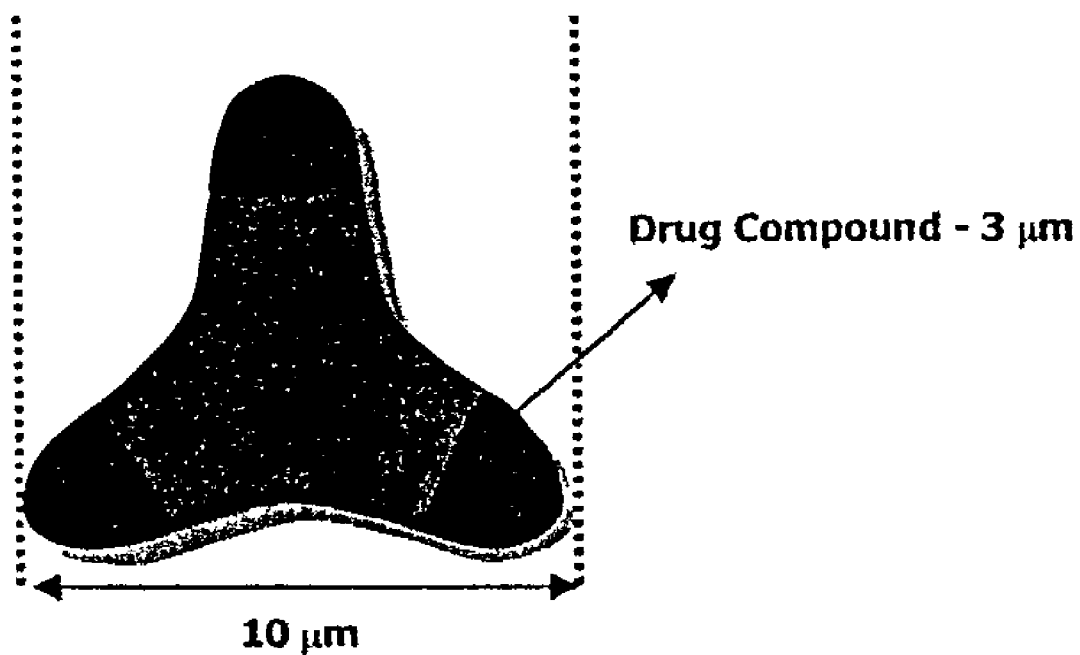
FIG. 9 is an example of an NDDS of the present invention having a tipped, trilobal morphology.
Figure 10:
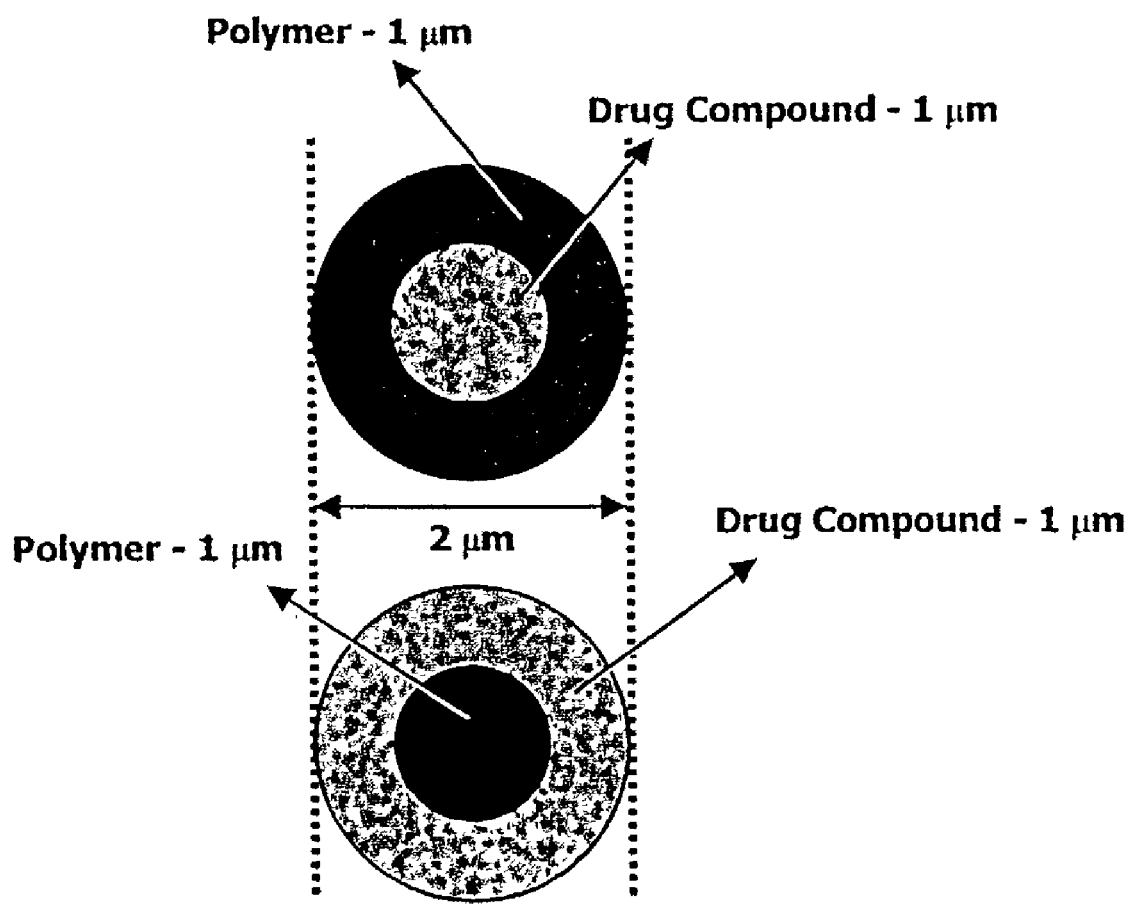
FIG. 10 is an example of an NDDS having a solid, sheath-core morphology.

A hollow sheath-core configuration is shown in FIG. 8. Alternatively, the drug may be at the tips of a trilobal fiber of the type shown in FIG. 9. A solid sheath-core structure is shown in FIG. 10. When the drug carrying polymer is in the sheath, the dissolution rate will be higher.

Figure 11:
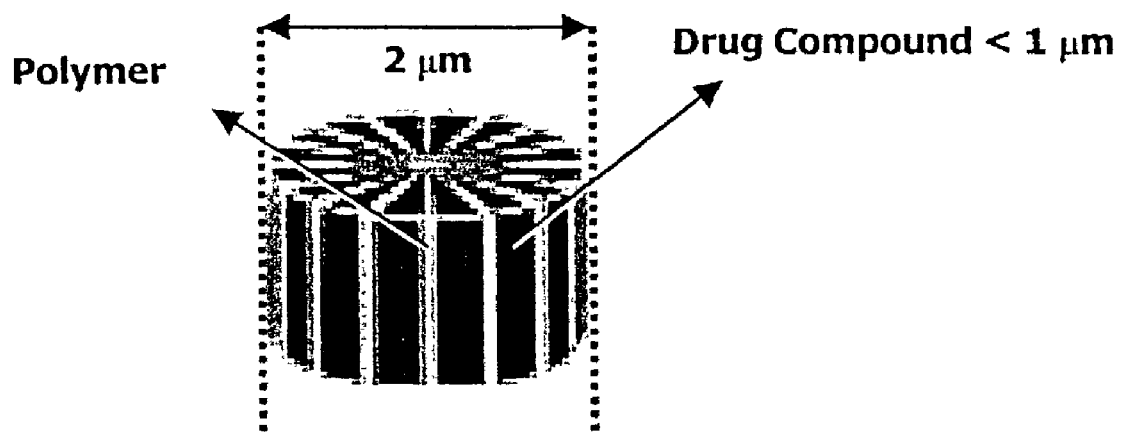
FIG. 11 is an example of a NDDS by using a solid, segmented pie morphology.

Segmented pie and hollow segmented pie configurations can lead to very useful structures where each segment may be less than one micron to facilitate dissolution. The segmented pie configuration is shown in FIG. 11.

Figure 12:
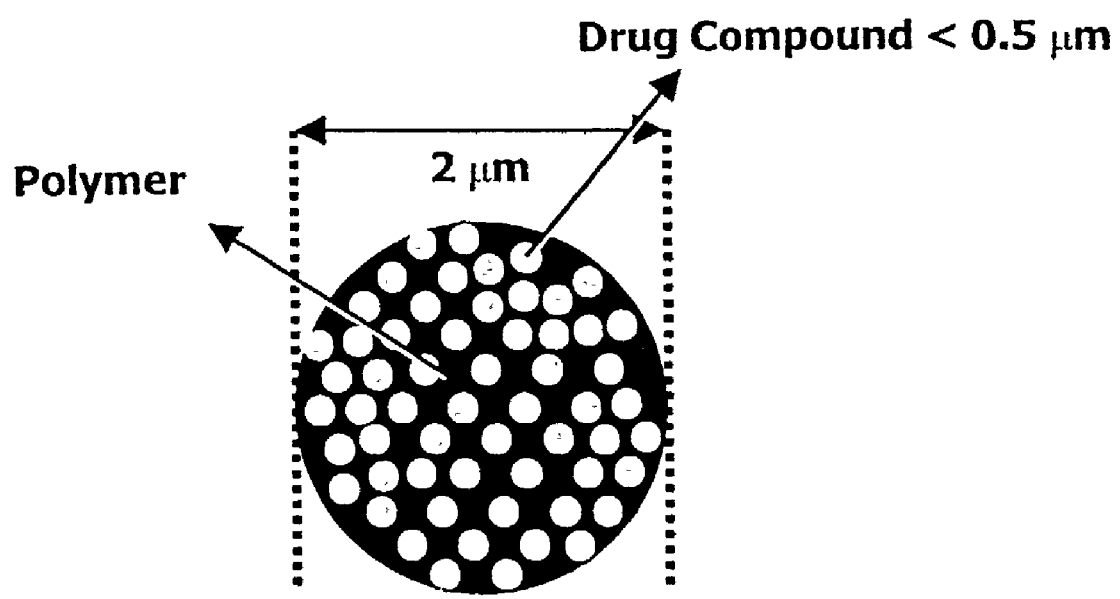
FIG. 12 is an example of a NDDS by using a solid, islands-in-the-sea morphology.
Figure 13:
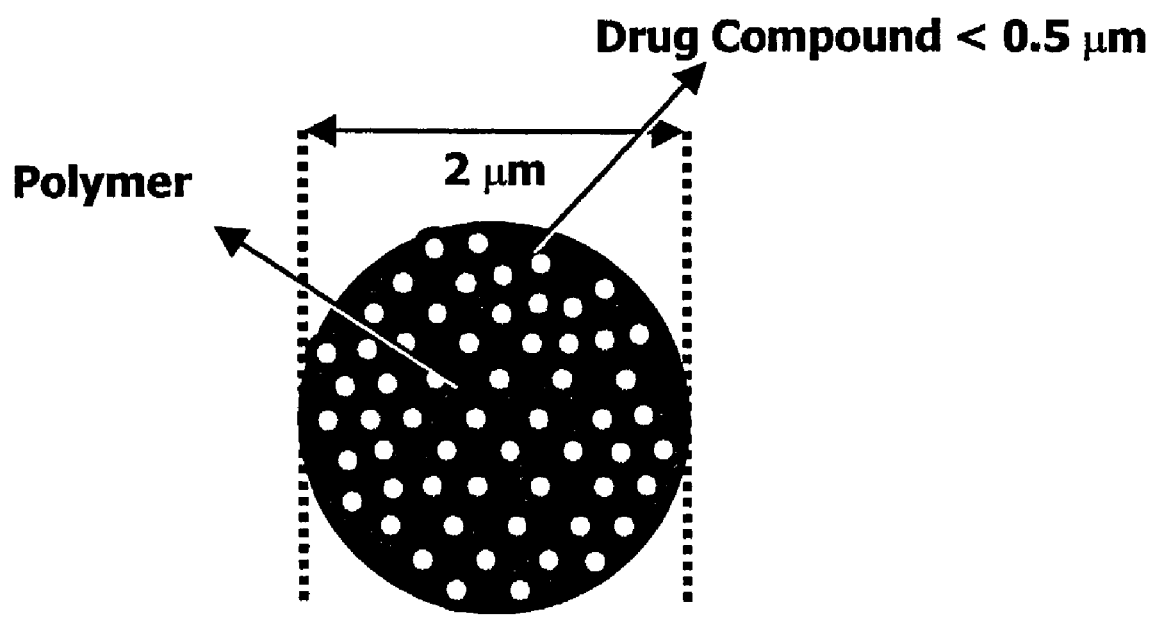
FIG. 13 is an example of a NDDS by using a solid, islands-in-the-sea morphology.

Smaller fibers can be achieved by using the islands in the sea configuration. The islands can be solid as shown in FIG. 12 or can be hollow as shown in FIG. 13.

Figure 14:
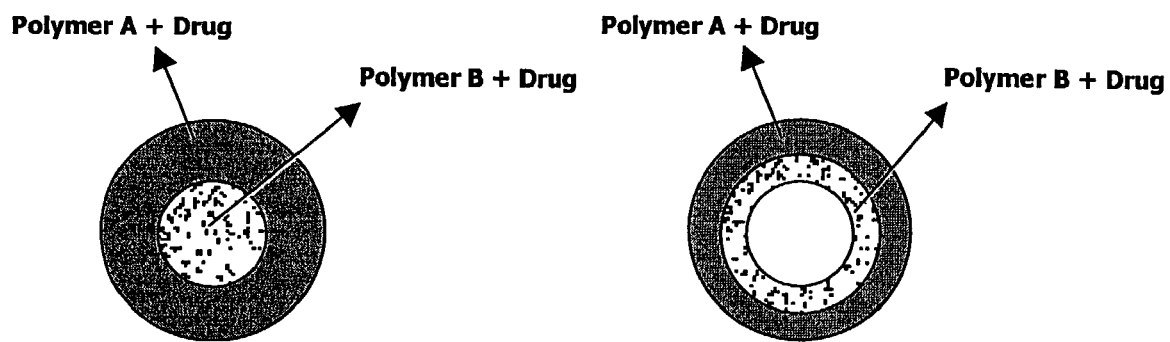
FIG. 14 is an example of a NDDS having two different polymers in the sheath and the core, wherein the drug has been added to both. The drug is available in the stomach and continues to be available for longer periods when it reaches the lower intestines if the pH sensitivity of the polymers and in the sheath and the core are carefully selected. These structures allow the formation of a long lasting drug where a single doze per day may be possible.

Longer lasting drug delivery systems can be created by a configuration such as the one shown in FIG. 14 where the sheath and the core both contain drugs in a suitable polymer carrier. The carrier polymers however, are different in their pH sensitivity or in their dissolution rate.

Figure 15:
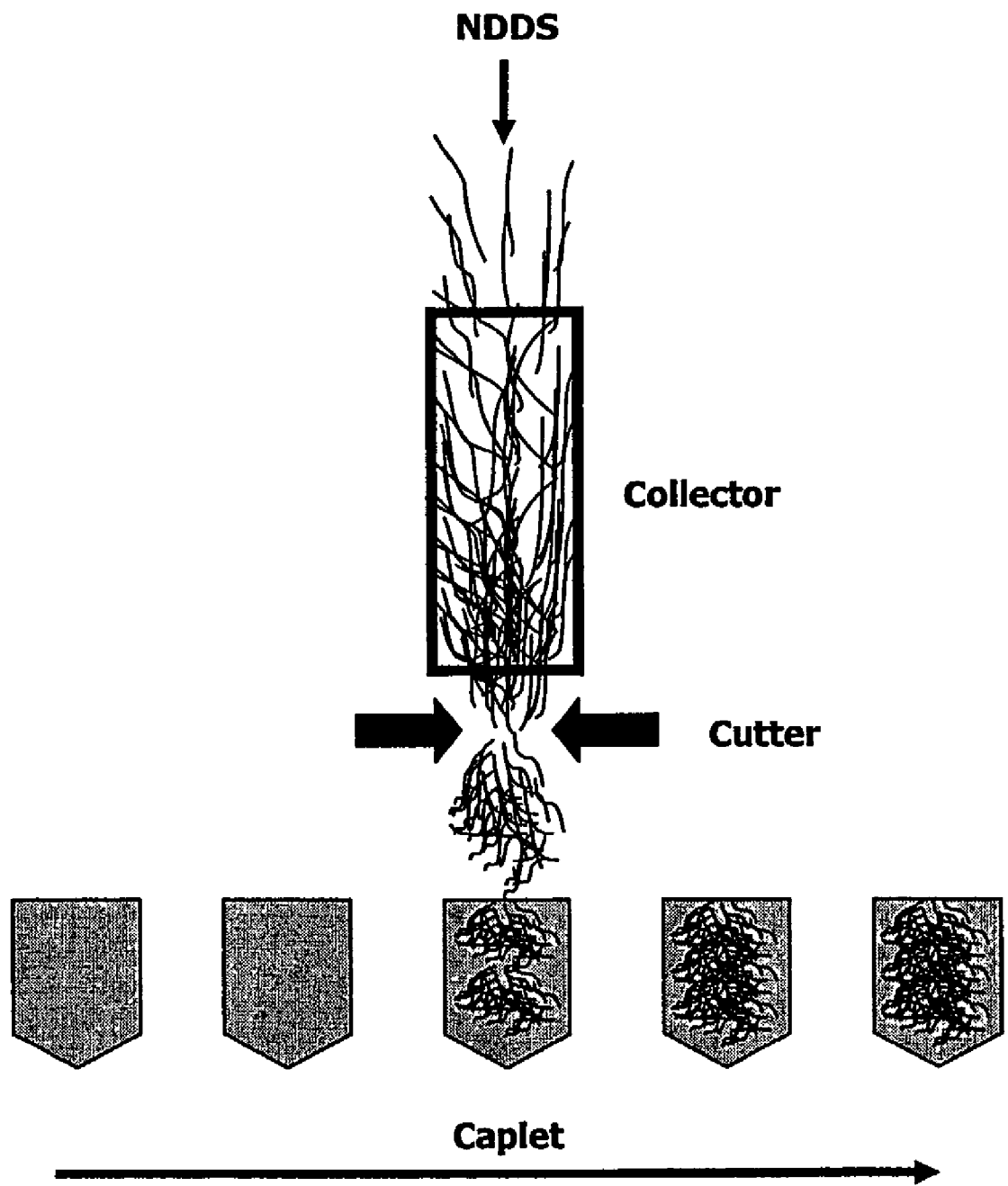
FIG. 15 is the schematic of a process for direct formation of tablets.
Figure 16:
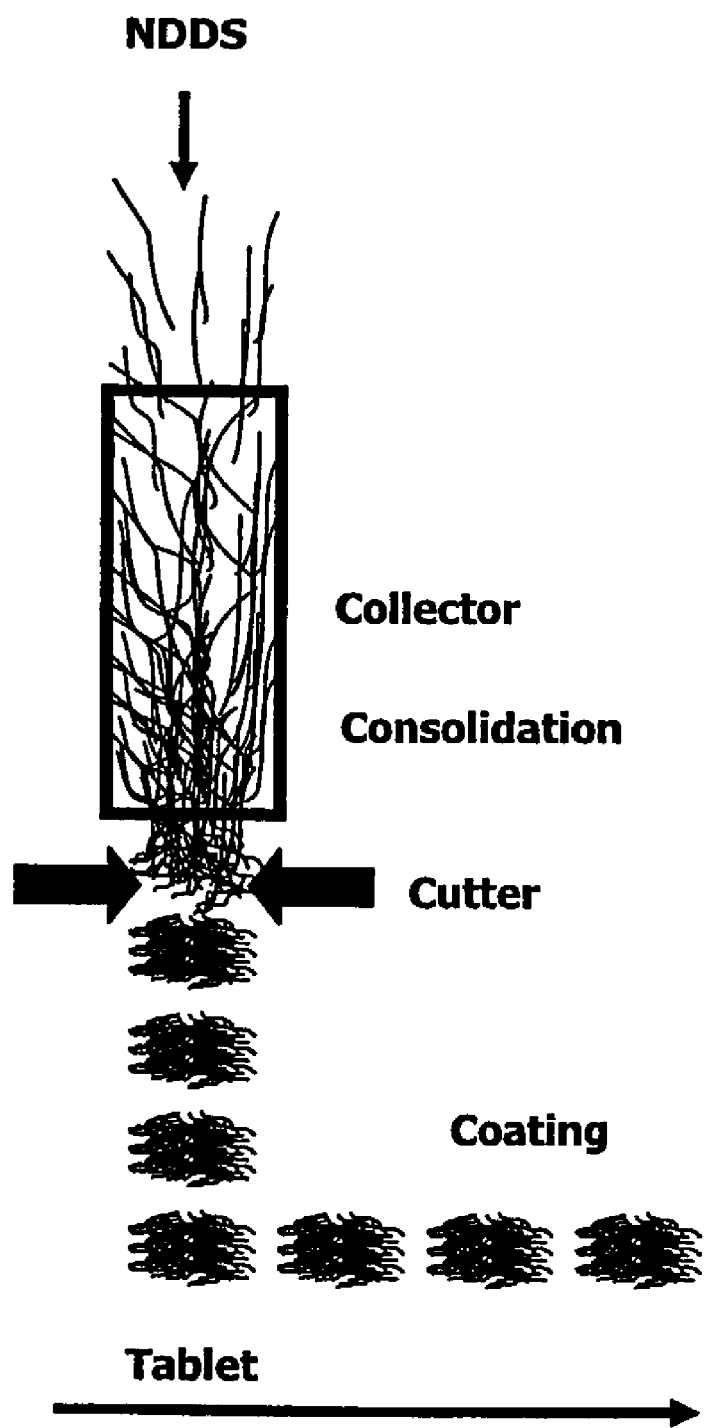
FIG. 16 is the schematic of a process for direct formation of tablets.

The formation of tablets directly from the spun fibers is possible by various means. The formation of capsules/caplets is possible by directly cutting the spun fibers and encasing them in the capsules/caplets as depicted in FIG. 15. Alternatively, the fibers can be compressed to form a consolidated fibrous structure that can then be cut and coated as shown in FIG. 16.

Figure 17:
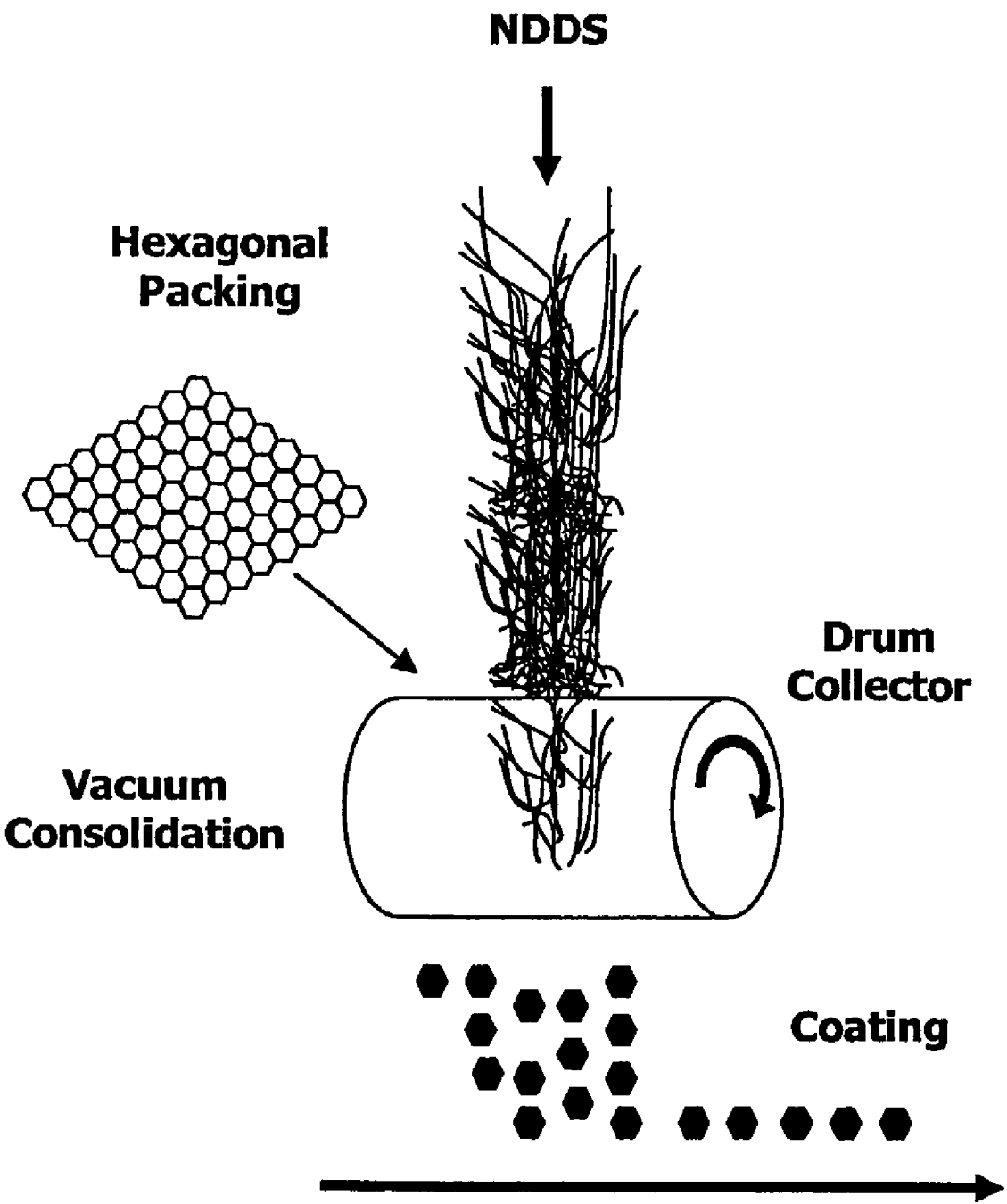
FIG. 17 is the schematic of the process for direct formation of tablets by using a drum former.

Another method for the manufacturing of the tablet directly from the extruded fibers is to collect these fibers in a drum formed with cavities of the shape desired for the tablets. This is demonstrated in FIG. 17. The fibers will be dispensed into the cavities and compressed by means of a vacuum system. A hexagonal grid pattern will lead to the least amount of waste.

Thus, the invention discovered is the process for making fibers carrying a drug and forming tablet or caplets or capsules from the same. The fibers are formed such to maximize dissolution rates and the delivery of the drug.

Further, the invention contemplates that the nanofibers can be formed to maximize the surface area of the fibers.

It will be understood that various details of the invention may be changed without departing from the scope of the invention. Furthermore, the foregoing description is for the purpose of illustration only, and not for the purpose of limitation—the invention being defined by the claims.

What is claimed is:

1. An ingestible, dissolvable extruded or meltblown nanofiber drug delivery system where the nanofibers are formed into tablets, the system consisting of water-soluble bicomponent fibers that include a first component of a biologically accepted polymeric binder and at least one drug and a second component of either a biologically acceptable polymer or a biologically acceptable polymeric binder and at least one drug where the overall concentration of the drug can be between about 10%-90% by volume fraction and where fibers therein can have any cross sectional shape and have a fiber diameter of about ten microns or less for providing an enhanced fiber surface area, the fibers selected from a group consisting of monofilament, multifilament or staple.

2. The fibers used in a drug delivery system according to claim 1 wherein the fibers are hollow.

3. The fibers used in a drug delivery system according to claim 1 wherein the fibers comprise a sheath/core cross-section, solid or hollow.

4. The structure of the fibers used in a drug delivery system according to claim 1 wherein the fibers are formed into a ribbon or stacked configuration.

5. The fibers used in a drug delivery system according to claim 1 wherein the fibers comprise a side by side cross-section.

6. The fibers used in a drug delivery system according to claim 1 wherein the fibers comprise an island in the sea cross-section, solid or hollow.

7. The fibers used in a drug delivery system according to claim 1 wherein the fibers comprise a segmented pie cross-section, solid or hollow.

8. The fibers used in a drug delivery system according to claim 1 wherein the fibers comprise more than 2 components.

9. A method for forming an ingestible, dissolvable tablet nanofiber drug delivery system from extruded or meltblown fiber consisting of water-soluble bicomponent fibers that include a first component of a biologically accepted polymeric binder and at least one drug and a second component of either a biologically acceptable polymer or a biologically acceptable polymeric binder and at least one drug where the overall concentration of a drug can be about 10% to 90% by volume fraction and where fibers therein can have any cross-sectional shape and have a fiber diameter of about ten microns or less for providing an enhanced fiber surface area and the fibers selected from a group consisting of monofilament, multifilament or staple, the method comprising the steps of forming the tablets directly from the fibers by directly cutting the spun fibers and then encasing them in the tablets.

10. A method for forming an ingestible, dissolvable tablet nanofiber drug delivery system from extruded or meltblown fiber consisting of water-soluble bicomponent fibers that include a first component of a biologically accepted polymeric binder and at least one drug and a second component of either a biologically acceptable polymer or a biologically acceptable polymeric binder and at least one drug where the overall concentration of a drug can be about 10% to 90% by volume fraction and where fibers therein can have any cross-sectional shape and have a fiber diameter of about ten microns or less for providing an enhanced fiber surface area and the fibers selected from a group consisting of monofilament, multifilament or staple, the method comprising the steps of compressing the fibers to form a consolidated fibrous structure and then cutting and coating the fibrous structure to form the tablets.

11. A method for forming an ingestible, dissolvable tablet nanofiber drug delivery system from extruded or meltblown fiber consisting of water-soluble bicomponent fibers that include a first component of a biologically accepted polymeric binder and at least one drug and a second component of either a biologically acceptable polymer or a biologically acceptable polymeric binder and at least one drug where the overall concentration of a drug can be about 10% to 90% by volume fraction and where fibers therein can have any cross-sectional shape and have a fiber diameter of about ten microns or less for providing an enhanced fiber surface area and the fibers selected from a group consisting of monofilament, multifilament or staple, the method comprising the steps of forming tablets directly from the fibers by collecting the fibers in a drum roller having cavities therein of the shape desired for the tablets, compressing the fibers by means of a vacuum system, and coating the compressed fibers to form the tablets.

* * * * *